United States Patent [19]

DiGiulio

[11] 4,139,945
[45] Feb. 20, 1979

[54] ORTHODONTIC ROTARY ANGULATING BRACKET ASSEMBLY

[76] Inventor: Hugo J. DiGiulio, 5623 Marshburn Ave., Arcadia, Calif. 91006

[21] Appl. No.: 779,012

[22] Filed: Mar. 18, 1977

[51] Int. Cl.² ............................................. A61C 7/00
[52] U.S. Cl. ..................................................... 32/14 A
[58] Field of Search ................. 32/14 A, 66; 200/336; 74/553

[56] References Cited

U.S. PATENT DOCUMENTS

| | | | |
|---|---|---|---|
| 1,588,039 | 6/1926 | Monosmith | 74/553 X |
| 2,379,011 | 6/1945 | Laskin | 32/14 A |
| 3,203,098 | 8/1965 | Petraitis | 32/14 A |
| 3,423,833 | 1/1969 | Pearlman | 32/14 A |
| 3,721,005 | 3/1973 | Cohen | 32/14 A |
| 3,925,893 | 12/1975 | Anderson | 32/14 A |

*Primary Examiner*—Louis G. Mancene
*Assistant Examiner*—John J. Wilson
*Attorney, Agent, or Firm*—Fred N. Schwend

[57] ABSTRACT

A rotatably adjustable orthodontic bracket assembly for correcting improperly positioned or angled teeth. A tooth band or bonding base is provided with a bearing in which a pivot element is mounted having at one end a flexible friction flange engaging the posterior side of the band or base and having an arch wire bracket at the other end engaging the anterior side of the band or base so that the bracket may be readily adjusted to a desired angular setting and retained in such setting during handling. Thereafter, the bracket is welded to the band or base and subsequently the band or base is cemented to the tooth. A gage is provided to readily adjust the bracket to any predetermined angular setting or to indicate the angle to which the bracket has been previously set.

3 Claims, 11 Drawing Figures

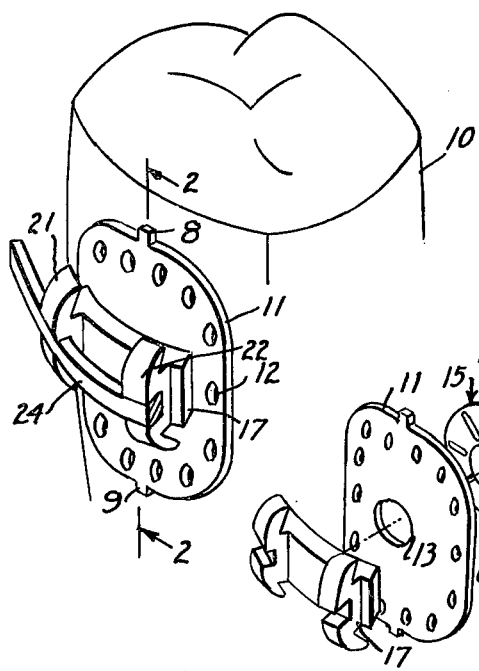
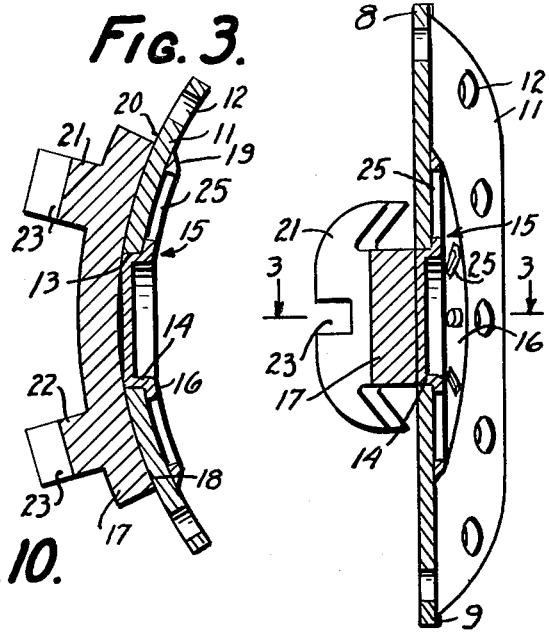
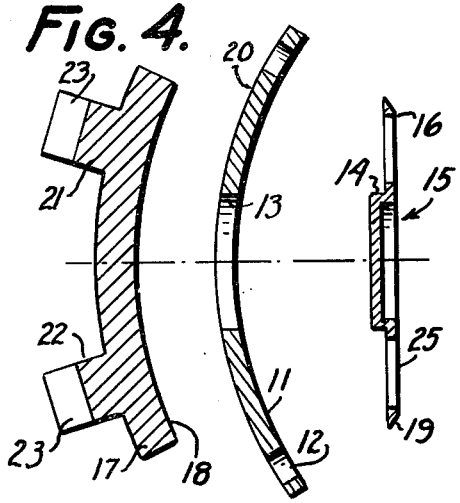
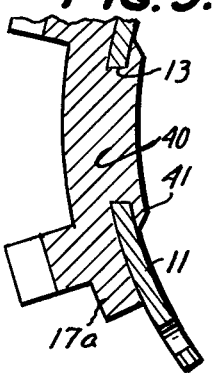
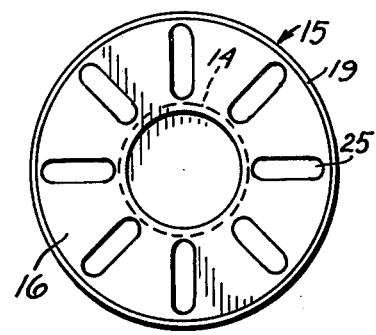
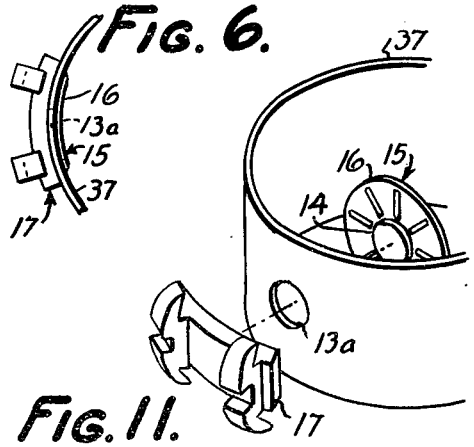
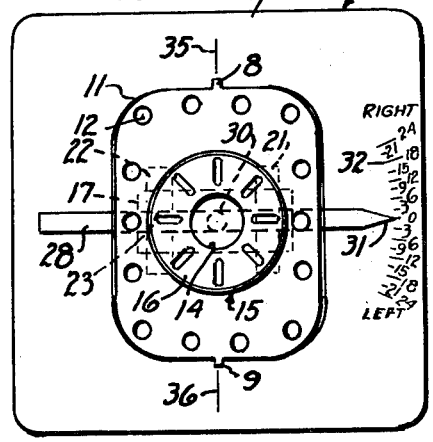
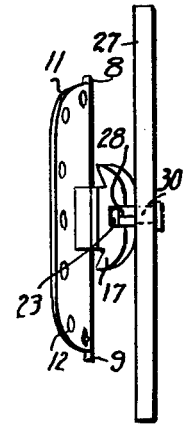

4,139,945

ORTHODONTIC ROTARY ANGULATING BRACKET ASSEMBLY

BACKGROUND OF THE INVENTION

1. Field of the Invention

This invention relates to orthodontic devices and has particular reference to devices for uprighting or angulating and otherwise correcting improperly positioned angled teeth for proper alignment.

2. Description of the Prior Art

According to the present general practice in uprighting and otherwise repositioning teeth along the dental arch, the orthodontist is provided with bonding bases or endless bands to be cemented to the teeth to be corrected. Such bases or bands are provided on their anterior sides with arch wire brackets which are welded at different angular settings. Thus, the orthodontist may select from an inventory of different assemblies a desired size and shape of base or band to fit a particular tooth, and also he must select an assembly having the arch wire bracket arranged at an appropriate angular setting or as near as possible to such setting in order to provide the desired amount of correction.

Obviously, the orthodontist must therefore carry a large inventory of different bracket assemblies in order to take care of all needs. Obviously also, in order to maintain the inventory at a practical limit, the bracket assemblies are normally available with the arch wire brackets set at certain angular increments only so that if assemblies are required with brackets at angular settings other than those normally supplies, such assemblies must be ordered specially from the manufacturer.

SUMMARY OF THE INVENTION

Accordingly, a principal object of the present invention is to provide an adjustable orthodontic arch wire bracket assembly which may be readily adjusted to any desired angular position.

Another object is to provide an adjustable orthodontic bracket assembly which is more compact, less expensive and more easily adjustable than prior assemblies of this type.

Another object is to provide an adjustable orthodontic bracket assembly which does not require the use of pins, screws or other mechanical elements to lock the same in place.

A further object is to provide a gage for facilitating adjustment of the arch wire bracket of an orthodontic assembly to different desired angular settings and/or to indicate such angular settings.

According to the invention, a bonding base or tooth band is provided with a bearing hole in which a pivot member is inserted, the latter having a flexible flange which frictionally engages the posterior side of the base or band and having an arch wire bracket engaging the anterior side of such base or band, thus forming a rotary angulating bracket assembly. Due to such frictional engagement, the bracket will be held in any adjusted position during subsequent handling. After the bracket assembly has been properly adjusted, the bracket is welded onto the base which is then cemented onto the tooth. The resulting assembly takes up substantially no greater space and presents no more projections than a standard non-adjustable bracket assembly.

A gage is provided comprising a gage member on which an angle indicating bar is pivoted. The latter may be coupled to the arch wire bracket to facilitate setting of the bracket to a desired angle relative to the tooth base or bar or to indicate the angle in degrees to which the bracket has been set.

BRIEF DESCRIPTION OF THE DRAWING

The manner in which the above and other objects of the invention are accomplished will be readily understood on reference to the following specification when read in conjunction with the accompanying drawing, wherein:

FIG. 1 is an enlarged perspective view illustrating one form of the invention as mounted on a tooth.

FIG. 2 is a further enlarged sectional elevation view taken along line 2—2 of FIG. 1.

FIG. 3 is a sectional plan view taken along line 3—3 of FIG. 2.

FIG. 4 is a sectional plan view, similar to FIG. 3, but exploded to illustrate the parts prior to assembly.

FIG. 5 is a rear view of the friction flange.

FIG. 6 is a plan view illustrating another form of the invention wherein the arch wire bracket is adjustably mounted on a tooth band.

FIG. 7 is a front view of an angle setting gage, illustrating an adjustable rotary angulating bracket assembly of the invention mounted thereon.

FIG. 8 is a side view of the gage and bracket assembly mounted thereon.

FIG. 9 is a sectional plan view, partly broken away, through a modified form of the invention.

FIG. 10 is an exploded perspective view of the form of invention shown in FIG. 1.

FIG. 11 is an exploded perspective view of the form shown in FIG. 6.

DESCRIPTION OF THE PREFERRED EMBODIMENT

Referring to the drawing, and particularly to FIGS. 1 to 5, the invention is disclosed therein as embodied with a thin, generally rectangular, bonding base member 11, preferably of stainless steel, having a series of openings 12 along its perimeter. The base 11 is curved about a vertical axis as seen in FIGS. 3 and 4 to generally conform to the anterior convex surface of a tooth, i.e., 10, to which the assembly is to be attached. Centering tips 8 and 9 are formed on the upper and lower edges, respectively of the base.

A bearing hole 13 is formed through the centeral portion of the base 11 to rotatably support a pivot portion or element 14 of a pivot member generally indicated at 15. The latter is formed of thin flexible material, such as stainless steel, having a thickness on the order from 0.0025 to 0.010 inches. The pivot portion 14 is preferably drawn from or otherwise integrally formed with a circular flange 16 which normally, prior to assembly, extends in a flat plane, as seen in FIG. 4. The flange 16 is preferably chamfered at 19 around its circumference.

During assembly, the pivot portion 14 of pivot member 15 is fitted in the bearing 13 and is welded to an arch wire bracket 17, the latter being curved at 18 to fit against and conform to the arcuate anterior surface 20 of the base 11. During such assembly, the flange 16 is distorted or forced to conform to the posterior curved surface of the base 11, as seen in FIGS. 2 and 3, to thus establish an adequate frictional engagement.

The bracket 17 is provided with spaced bosses or wings 21 and 22 in which aligned slots 23 are formed to receive an arch wire 24.

Equi-angularly spaced slots 25, as best seen in FIG. 5, are formed in the flange 16 of pivot member 15, such slots radiating outwardly from the pivot portion 14 to enhance or increase the flexibility of the flange and also to provide openings for receiving cement as will be described presently.

Accordingly, the rotary angulating bracket assembly including the pivot member 15 and arch wire bracket 17 may be readily adjusted relative to the base 11 to any desired angular setting and it will remain in such setting during handling, prior to being welded to the base.

FIGS. 7 and 8 illustrate a gage, generally indicated at 26, for adjusting the arch wire bracket 17 to any selected angular setting relative to the base 11 and for indicating such setting in angular degrees. The gage 26 comprises an indicator member or plate 27 and an indicator bar 28 having a width such that it will snugly fit within the arch wire slots 23 of bracket 17. The bar is pivotally mounted at 30 on the plate 27 and has a pointed end 31 moveable over an indicia scale 32 which is marked off in angular degrees.

In order to conveniently adjust the angular setting of the bracket 17 relative to the base 11, the bracket assembly is applied to the plate 27 with the bracket 17 facing the plate and with the arch wire slots 23 fitted over the bar 28. The base 11 is then held in a centered position with the axis of the pivot portion 14 coincident with the axis of the pivot 30 of the indicator bar 28 by locating the centering tips 8 and 9 in alignment with marker lines 35 and 36, respectively, formed on the plate 27. The bar 28 is then adjusted to a desired angular setting as indicated on the scale 32 to likewise adjust the bracket 17 to a corresponding angular setting to the left or right of a medial vertical location.

In mounting the adjusted bracket assembly to the tooth, i.e., 10, the orthodontist first spot welds the bracket 17 to the base 11 at points adjacent the outer extremities of the bracket. Thereafter, he applies cement to the posterior surfaces of the base 11 and flange 16 and applies the assembly to the tooth 10 until the cement cures. In this case, the cement will enter the openings 12 and slots 25 to establish a firm bond to the tooth.

FIG. 6 illustrates the invention as incorporated with an endless band 37 which forms a base member and which is intended to completely surround the tooth. In this case, a bearing 13a is formed in the band 37 and the pivot member 15 and arch wire bracket 17 are assembled to the band in the same manner as described in connection with the base 11 in FIGS. 1 to 5. Here also, after angularly adjusting the bracket 17, it is welded to the band 37 and the assembly cemented to the tooth. Cement entering the slots in the flange 16 will aid in locking the assembly to the tooth surface.

FIG. 9 illustrates a modified form of the invention wherein an arch wire bracket 17a, somewhat similar to bracket 17, i provided with a centrally located pivot formation 40 which journaled in the bearing hole 13 in the base 11 and is peened or otherwise formed into a thin flange 41 which frictionally engages the base 11 to hold the bracket 17 in different adjusted positions.

From the foregoing, it will be seen that the present invention provides an inexpensive and compact adjustable or angulating arch wire bracket assembly which is easy to adjust to any desired setting and to secure in place. It does not appreciably increase the size of the assembly beyond that of a non-adjustable arch wire bracket assembly and is devoid of any projecting parts which might otherwise interfere with the comfort of the patient.

Also, the invention reduces the amount of equipment needed by the orthodontist to prepare a bracket assembly and, further, it enables the orthodontist to allocate most of the work of preparing the bracket assembly to a less experienced person. For example, the orthodontist may note on a suitable tray or chart the identifying number of each tooth to be corrected, the particular size and shape of the base or band for such tooth and the angle to which the associated bracket is to be set. With this information, an assistant can prepare the bracket assemblies and later the orthodontist need only mount the assemblies on the teeth.

It will be obvious to those skilled in the art that many variations may be made in the exact construction shown without departing from the spirit and scope of the invention as defined by the appended claims. For example, in lieu of welding the bracket 17 to the base 11 or to the band 37, the orthodontist could rely on the cement to secure the flange 16, and therefore the bracket 17, in place when securing the assembly onto the tooth.

I claim:

1. An adjustable orthodontic bracket assembly comprising
    a base member for attachment to a tooth,
    the side of said base member facing said tooth being curved,
    said base member having a bearing opening extending therethrough,
    a pivot element pivotal in said bearing,
    a thin, flexible flange integral with said pivot element on said side of said base member facing said tooth,
    and an arch wire bracket integral with said pivot element on the opposite side of said base member,
    said bracket having means for coupling to an arch wire,
    said base member flexing said flange whereby to retain said pivot element in different angularly adjusted positions relative to said base member,
    said flange having openings therethrough whereby to increase the flexibility of said flange and to receive the cement for attaching said assembly to said tooth.

2. An adjustable orthodontic bracket assembly as defined in claim 1 wherein said openings comprise radially extending slots.

3. An adjustable orthodontic bracket assembly as defined in claim 1 comprising
    an indicator member,
    an indicator bar,
    means other than said pivot element pivotally supporting said bar on said indicator member, and indicia on said indicator member for indicating the position of said bar relative to said indicator member,
    said coupling means being effective to couple said bar to said bracket whereby pivotal movement of said bar will cause similar pivotal movement of said bracket.

* * * * *